United States Patent [19]

Aldred

[11] Patent Number: 4,936,152
[45] Date of Patent: Jun. 26, 1990

[54] PIPETTE TIP STORAGE TRAY AND METHOD OF USE

[76] Inventor: Dennis A. Aldred, 274 Cottage Hill, Elmhurst, Ill. 60126

[21] Appl. No.: 357,770

[22] Filed: May 30, 1989

[51] Int. Cl.$^5$ ............................................. B01L 3/02
[52] U.S. Cl. .................................................. 73/863.32
[58] Field of Search ........... 73/863.32, 864.01, 864.11, 73/864.17, 864.21–864.25; 422/99, 100, 104; 206/562, 486; D24/29, 31, 32, 55

[56] References Cited

U.S. PATENT DOCUMENTS

| | | | |
|---|---|---|---|
| Re. 27,637 | 5/1973 | Roach | 422/100 |
| 3,853,217 | 12/1974 | Scordato et al. | |
| 4,215,092 | 7/1980 | Suovaniemi et al. | 73/863.32 |
| 4,349,109 | 9/1982 | Scordato et al. | |
| 4,478,094 | 10/1984 | Salomaa et al. | 73/863.32 |

OTHER PUBLICATIONS

Labindustries Today Brochure, Aug. 1983.

*Primary Examiner*—Robert Raevis
*Attorney, Agent, or Firm*—Irwin C. Alter

[57] ABSTRACT

A pipette tip storage tray and method of use. The tray comprises a frame which includes means for positioning the pipette tips in the storage tray in a biaxial array, so that the pipette tips are uniformly spaced along a first axis with a first spacing and along the second axis with a second spacing. Thus, the pipette tips can be engaged by a first, multi-tip pipettor along the first axis to pick up a plurality of pipette tips along the first axis and to transfer them for pick up or dispensing of liquid to a first multiple-well sample tray. The pipette tips may also be picked up along their second axis, transverse to the first axis, by a second, multi-tip pipettor of different spacing, for transfer to a second multiple-well sample tray of different dimensions from the first tray.

9 Claims, 3 Drawing Sheets

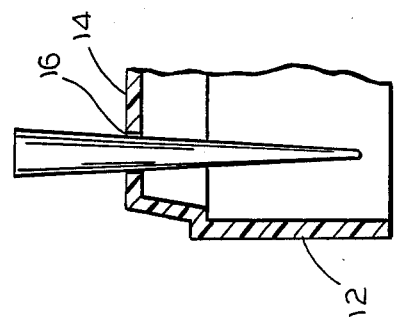
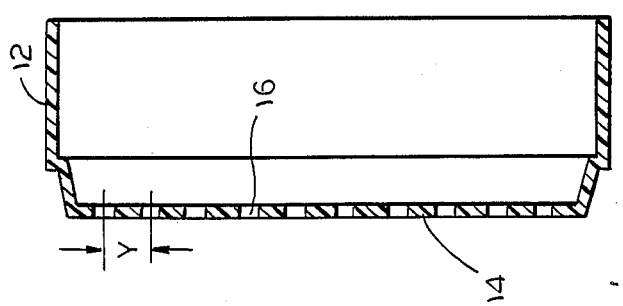
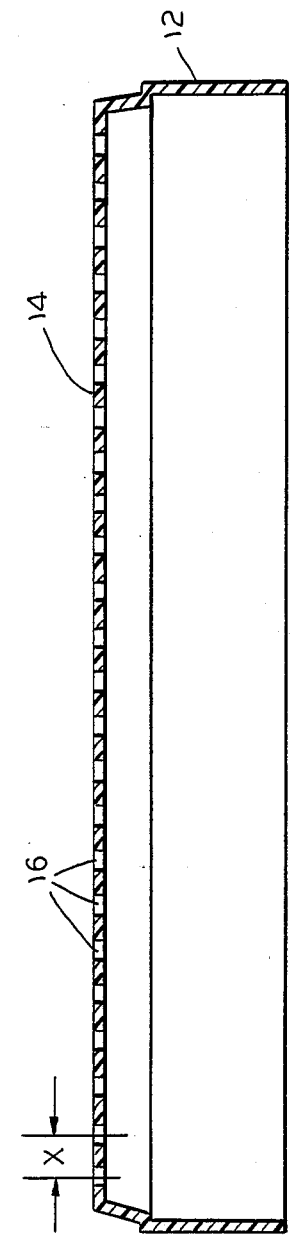
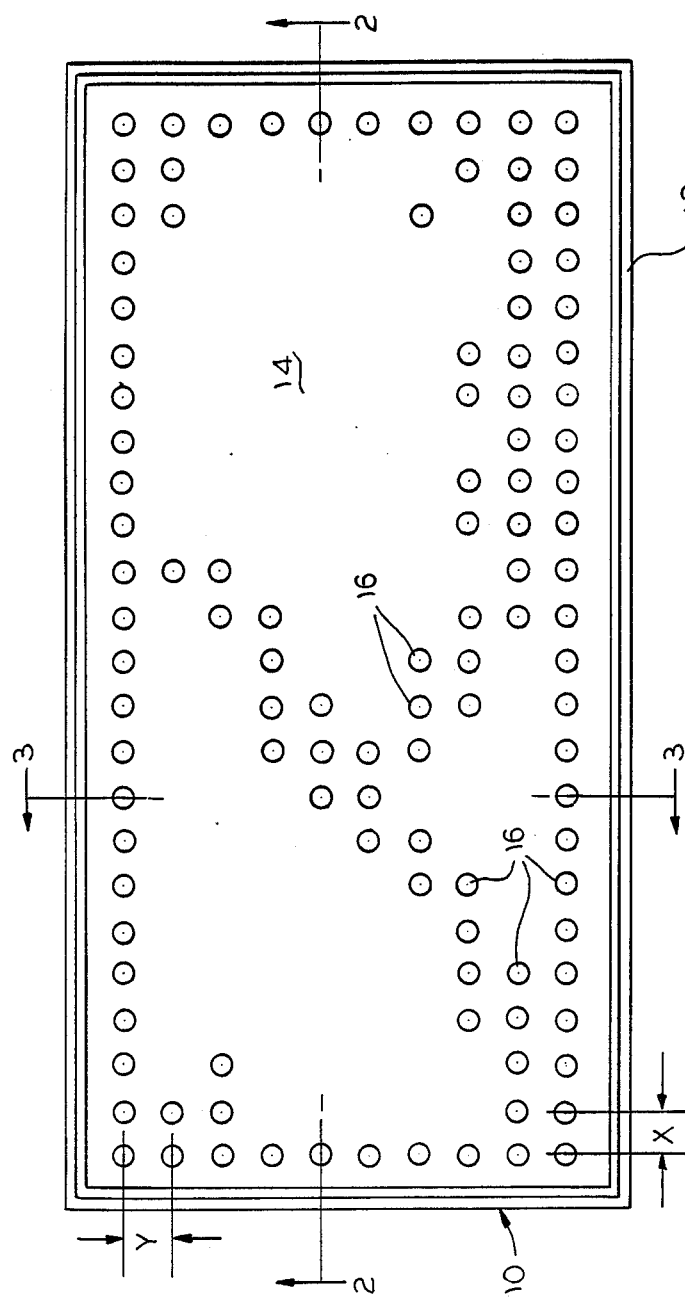

PIPETTE TIP STORAGE TRAY AND METHOD OF USE

BACKGROUND OF THE INVENTION

Disposable pipette tips and trays for carrying them are widely used in clinical laboratories and the like, and are also widely described in the patent literature, including Scordato et al. U.S. Patent Nos. 3,853,217 and 4,349,109, for example.

Disposable pipette tips are typically provided to the user in a large package, in which the pipette tips, which are typically very small, are held in an array with the respective larger open ends of the pipette tips all being disposed approximately in a single plane, to permit engagement by a multi-tip pipettor to engage and pick up a linear plurality of the pipette tips and to transfer them to the respective sample wells of a multiple-well sample tray. There, they are used to pick up and/or dispense liquids to help constitute whatever assay or diagnostic procedure may be taking place in each sample well of the multiple-well sample tray.

All of the above technology is widely commercially available, with various designs of apparatus being available for accomplishing the pipette tip transfer to their sites of use for purposes of facilitating typical diagnostic assays or determinations.

There are commercially available multi-tip pipettors apparatus for picking up a linear array of pipette tips and transferring them to their desired sites of use. However, the individual spacing between pipette tips in their storage package must be specific and predetermined in order for a given commercially available multi-tip pipettor apparatus to properly engage the pipette tips and to subsequently transfer them at their site of use.

Accordingly, in the prior art, a specific pipette tip storage tray generally must be used with a specific model of multi-tip pipettor. Thus, operations in a laboratory can be greatly hampered if it turns out that the wrong type of storage tray is present, if that tray is incompatible with the particular multi-tip pipettors used in that laboratory. Thus, laboratory personnel must order different models of pipette tip storage trays to accommodate different models of multitip pipettors which are currently in use. This requires a more complex ordering program, with increased space and attention to the inventory of such different pipette tip storage trays.

In accordance with this invention, a pipette tip storage tray is provided, and a method for using it, in which different models of multi-tip pipettors, adapted for use with differently spaced rows of pipette tips, may be supplied by a single pipette tip storage tray. Thus, the ordering and inventory process of laboratories may be significantly simplified, since different models of multi-tip pipettors may be used to engage pipette tips and to transfer them to their position of use from the same tray. However, this may be accomplished at essentially no increase in cost, and with great simplicity of structure.

DESCRIPTION OF THE INVENTION

In this invention, a pipette tip storage tray comprising a frame and pipette tip positioning means. By this invention, the positioning means is adapted to position pipette tips in the storage tray in a biaxial array. The pipette tips are uniformly spaced along a first axis with a first spacing which permits the pipette tips to be engaged by a first, multi-tip pipettor, to engage and pick up a plurality of pipette tips along the first axis and to transfer them to their place of use in a first multiple-well sample tray.

The pipette tips carried in the storage tray are also uniformly spaced along a second axis which is transverse to the first axis. The second axis has a second spacing of pipette tips which is different from the first spacing along the first axis. This permits the same pipette tips in the same array to be engaged by a second, differently spaced, multi-tip pipettor, to engage and pick up a plurality of pipette tips along the second axis, and to transfer them to their place of use in a second multiple-well sample tray. The first and second multiple-well sample trays are adapted to receive the respective pipette tips of differing spacing from the respective multi-tip pipettors.

Thus, the tray of this invention can be used to service at least two different multi-tip pipetting systems, so that any given laboratory or hospital can use both of said systems, and may draw the pipette tips from a common supply tray. In fact, it is possible for a first of the multi-tip pipettors to draw pipette tips from a given tip storage tray of this invention, and then for the second multi-tip pipettor to draw pipettes from the same tray, each drawing pipette tips having differing spacing from along the respective axis of pipette tips in the tray that is suitable for the given multi-tip pipettor.

Preferably, the pipette tip storage tray of this invention defines a first pipette tip spacing along the first axis which is essentially 9.05 mm., measured between centers of the respective pipette tips carried in the tray along the first axis. Also, the same pipette tip storage tray of this invention preferably defines a second pipette tip spacing along the second axis of substantially 9.8 mm., on a similar center-to-center basis as described above.

The pipette tip storage tray of this invention may define a wall as part of a frame which, in turn, defines a plurality of individual pipette tip-receiving apertures. The apertures are arranged along the first axis with the first spacing and the second axis with the second spacing. Preferably, the first and second axes are perpendicular to each other, although, if desired, a slightly denser packing pattern of pipette tips may be provided, in which the first and second axes are at an acute angle to each other, for example about 30 degrees.

Thus, one may use with a preferred embodiment of the tray of this invention either of two commercially available multi-tip pipettors and multiple-well sample trays that go with the pipettors. One simply selects the desired pipettor, specific commercially available pipettors being adapted for pipette tip spacings of 9.05 or 9.8 mm. One orients the multi-tip pipettor chosen along the appropriate axis of pipette tips in the storage tray of this invention, and accordingly engages the pipette tips in normal manner. Then, the pipette tips are withdrawn from the storage tray and moved to a multiple-well sample tray in accordance with conventional practice, where they are used in normal manner to pick up and/or dispense liquids to facilitate diagnostic assays and determinations.

DESCRIPTION OF DRAWINGS

In the drawings, FIG. 1 is a plan view of a pipette tip storage tray in accordance with this invention;

FIG. 2 is a sectional view taken along line 2—2 of FIG. 1;

FIG. 3 is a sectional view taken along line 3—3 of FIG. 1;

FIG. 4 is a fragmentary sectional view showing the pipette tip storage tray of this invention carrying a pipette tip in one of its apertures;

DESCRIPTION OF SPECIFIC EMBODIMENTS

Figure 5:
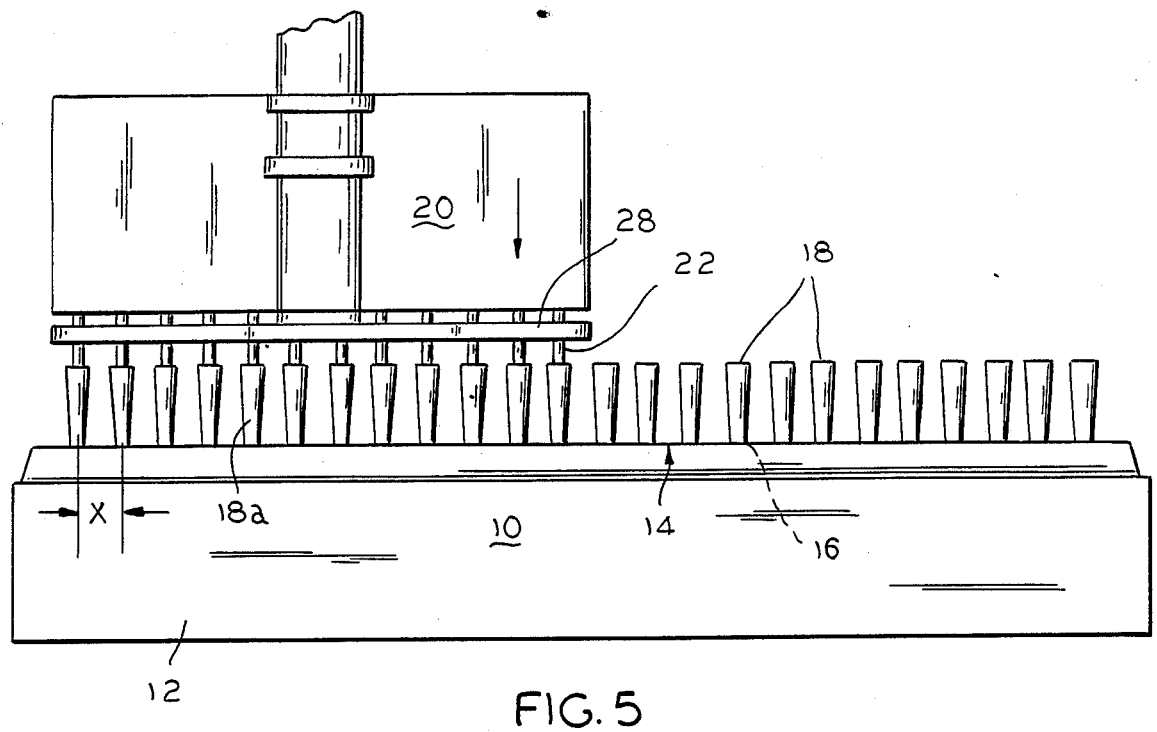
FIG. 5 is an elevational view of the pipette tip storage tray of FIG. 1, carrying pipette tips, with one model of a multi-tip pipettor picking up a linear plurality of pipette tips from the tray along a first axis.

Referring to FIGS. 1 through 4, a pipette tip storage tray 10 in accordance with this invention is disclosed.

Tray 10 defines a frame or side wall 12 which includes an integral bottom wall 14. Bottom wall 14, in turn, includes an array of apertures 16, the particular array of apertures shown being a rectangular, biaxial array of apertures which extend along a first axis X, and also extending along a second axis Y, the two axes X, Y being perpendicular to each other. As shown in FIG. 4, the array of apertures 16 may be filled with pipette tips 18 which project through the apertures, to thus form an array of pipette tips which are of the identical dimensions and positioning as the array of individual apertures 16. Specifically, the center-to-center spacing of each of the pipettes 18 along the X axis is essentially 9.05 mm., while the center-to-center spacing between the respective pipette tips along the Y axis of the same array is 9.8 mm.

Figure 7:
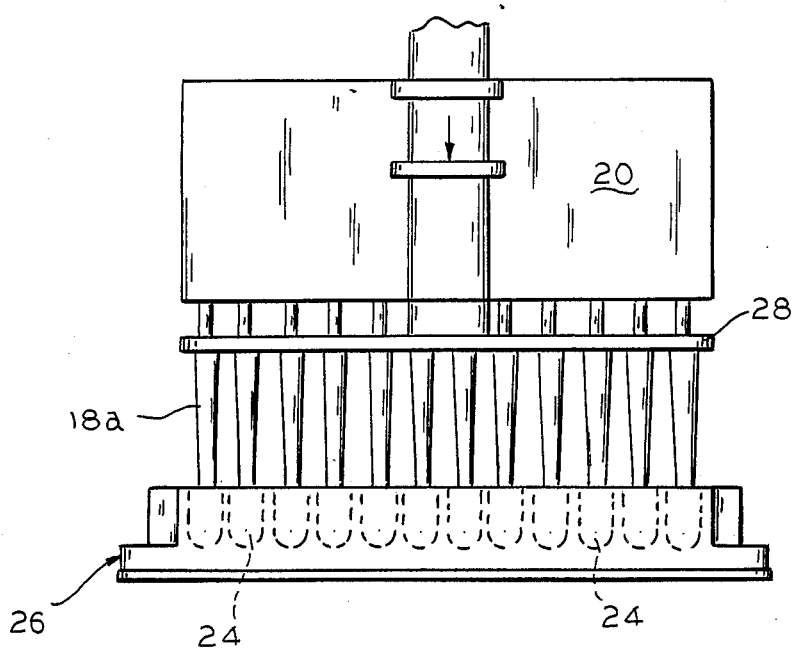
FIG. 7 is an elevational view of the multi-tip pipettor of FIG. 5, shown in the process of transferring its linear plurality of pipette tips to a first multiple-well sample tray.

Accordingly, a storage tray 10 in accordance with this invention, which is partially or completely filled with pipette tips 18, is shown in FIG. 5 to be receiving a first, conventional, multi-tip pipettor 20, which is in the process of engaging a linear array of pipette tips 18a by advancing of a linear array of nose 10 cones 22 into the tapered bores of the conventional pipette tips 18a, to provide temporary frictional engagement. Following this, pipettor 20 will be withdrawn, along with the engaged pipette tips 18a, and the pipette tips 18a will be transferred by pipettor 20 to a plurality of recesses 24 in a first sample tray 26, as shown in FIG. 7 where liquid can be drawn up into the tips or dispensed from the tips. When a reagent or liquid is drawn up into the tips, the pipettor 20 moves the filled tips to an appropriately spaced multiple-well sample or test tray and releases the liquid into the appropriately spaced wells. There, the pipette tips 18a will be used in conventional manner for preparing a microvolume diagnostic or screening test, or the like.

Figure 8:
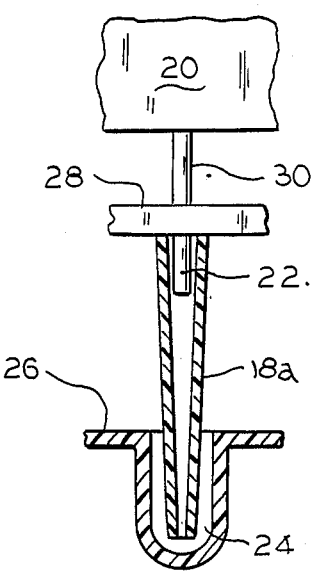
FIG. 8 is an enlarged, fragmentary elevational view, taken partly in section, showing the pipettor of FIG. 7 in the process of releasing the liquid contents of a pipette tip into a recess of the first multiple-well sample tray.

As previously stated, the spacings of pipette tips 18a along axis X is 9.05 mm., as governed by the spacing of apertures 16 along the X axis. Multi-tip pipettor 20 may be of a readily available commercial design of pipettor in which nose cones 22 are similarly spaced essentially 9.05 mm. apart in linear array, so that they may easily engage pipette tips 18a along the X axis for use in accordance with that described above and as illustrated in FIGS. 5, 7 and 8.

Figure 6:
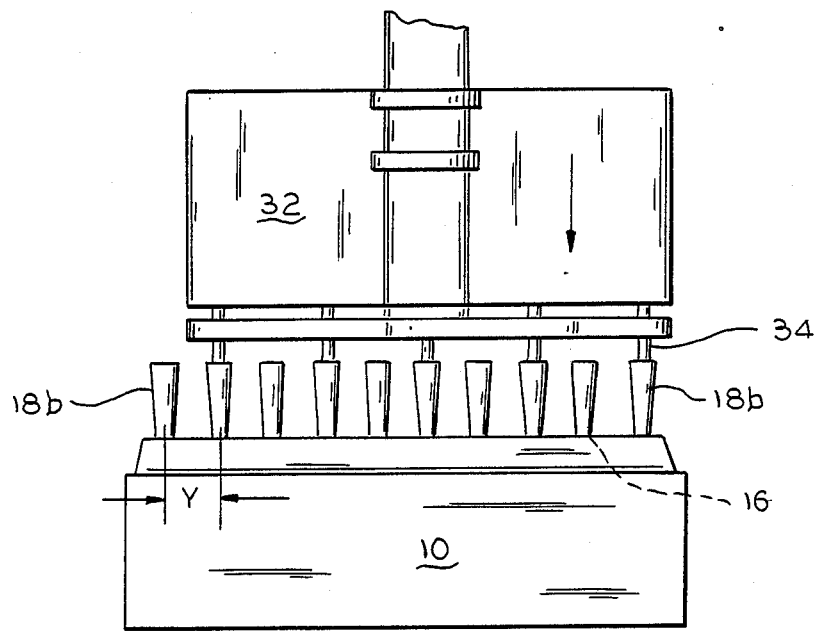
FIG. 6 is an elevational view, taken perpendicular from the view of FIG. 5, of the pipette tip storage tray of FIG. 5 in which another model of multi-tip pipettor is picking up a linear plurality of pipette tips from the tray along a second axis, which axis is perpendicular to the first axis.
Figure 9:
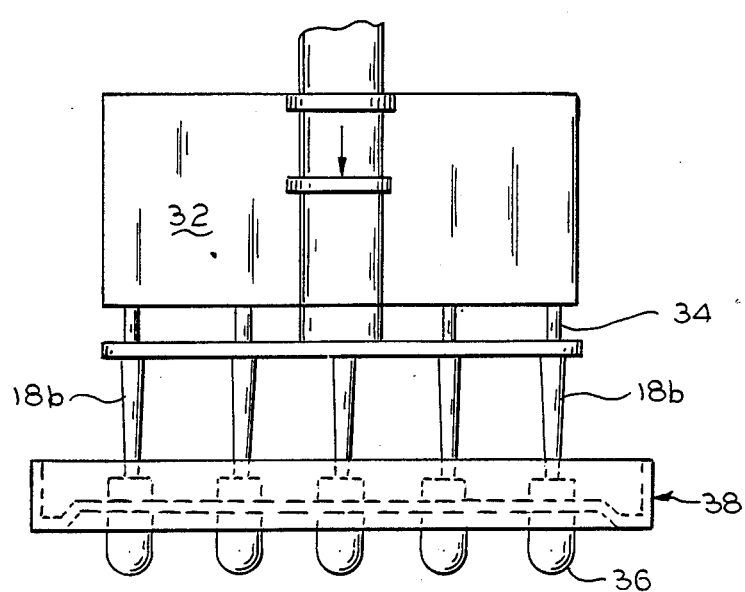
FIG. 9 is an elevational view showing the second pipettor of FIG. 6 releasing the liquid contents of its pipette tips into the recesses of a second multiple-well sample tray.
Figure 10:
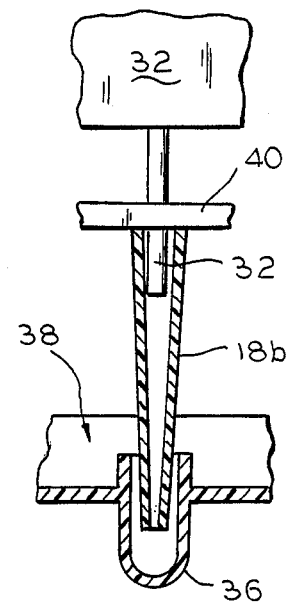
FIG. 10 is an enlarged, fragmentary elevational view, taken partly in section, showing the operation illustrated in FIG. 9 in added detail.

On the other hand, another model of conventional multi-tip pipettor 32 is shown in FIG. 6. This pipettor carries a linear array of nose cones 34, analogous to nose cones 22 in the embodiment of FIG. 5, which are positioned to engage a linear array of pipette tips 18b along the Y axis, as shown in FIG. 6. In this particular embodiment of pipettor 32, which is another readily commercially available type, the spacing of the respective nose cones 34 is twice that of the spacing of pipette tips 18b along the Y axis: 19.6 mm. Thus, as in the situation of FIGS. 5, 7, and 8, multi-tip pipettor 32 frictionally engages alternate pipette tips 18b along the Y axis by means of nose cones 34, and transfers them as in FIG. 9 to receptacles 36 of a second design of multiple-well sample tray 38 (for drawing or dispensing of liquid in the sample tray 38), which is compatible with multi-tip pipettor 32, as shown in FIG. 10. Afterward the advancement of plate 40 about each nose cone 34 can force each pipette tip 18b out of frictional engagement with each nose cone 34, to enable disposal of each pipette tip 18b.

Accordingly, it can be seen that the tray 10 of this invention can be used to provide a supply of pipette tips to two different commercial, multi-tip pipettor systems 20, 32 and their corresponding multiwell sample trays 26, 38. Thus, inventory problems are significantly reduced since both multi-well pipettors make use of the same supply tray. Additionally, it can be seen that tray 10 can also be compatible with other multi-tip pipettors which have different dimensions which are even fractions or multiples of the spacings of apertures 16 along either the X or the Y axis. Specifically, a multi-tip pipettor similar to 32 but with twice as many evenly spaced nose cones 34 could be used to collect pipette tips 18b along the Y axis. Likewise, pipettor system 20 could utilize nose cones 22 which are spaced two or three times as far apart as shown, while still being capable of collecting pipette tips 18a from along the X axis. Heretofore, multi-tip pipettors have engaged sequential tips in the linear array. The tray 10 in one axis, causes every other tip to be engaged, thereby reducing the space required to store a given number of tips.

The above has been offered for illustrative purposes only, and is not intended to limit the scope of the invention of this application, which is as defined in the claims below.

That which is claimed is:

1. In a pipette tip storage tray comprising a pipette tip positioning means, the improvement comprising, in combination:

said positioning means being adapted to position pipette tips in said storage tray in a biaxial array, said pipette tips being uniformly spaced about 9.05 mm. apart along a first axis to provide a first spacing which permits said pipette tips to be engaged by a first, multi-tip pipettor, to pick up a plurality of pipette tips along said first axis and to transfer them to a first multiple-well sample tray for drawing up or dispensing liquids; said pipette tips carried in the storage tray being also uniformly spaced 9.8 mm. apart along a second transverse to the first axis, in a second spacing permits said pipette tips to be engaged by a second, differently spaced multi-tip pipettor to pick up a plurality of pipette tips along said second axis to transfer them to a second multiple-well sample tray.

2. The pipette tip storage tray of claim 1 in which said positioning means includes a wall defining a plurality of individual pipette tip receiving apertures, said apertures being arranged along said first axis with said first spacing and said second axis with said second a spacing 3. The pipette tip storage tray of claim 2 in which said first and second axes are perpendicular to each other.

4. In the method of engaging a linear plurality of pipette tips in a storage tray with one of first and second different multi-tip pipettors, each pipettor being adapted to engage pipette tips having differing spacings, the improvement comprising, in combination:

said storage tray carrying pipette tip positioning means which are adapted to position pipette tips in said storage tray in a biaxial array, said pipette tips being uniformly spaced along a first axis with a first spacing which permits said pipette tips to be engaged by said first multi-tip pipettors to pick up a plurality of pipette tips along said first axis; said pipette tips carried in the storage tray being also uniformly spaced along a second axis, transverse of the first axis, with a second spacing different from the first spacing, which permits said pipette tips to be engaged by a second, differently spaced multi-tip pipettor to pick up a plurality of pipette tips along said second axis; and including the step of orienting a linear plurality of pipette tips in said tray extending along one of said first and second axes with one of said first and second pipettors, and engaging and removing from the storage tray said linear plurality of pipette tips with said one pipettor, to transfer the engaged pipette tips to a multiple-well sample pipette tray.

5. The method of claim 4 in which, sequentially, the first and second multi-tip pipettors are used to engage and remove pipette tips from said storage tray, each pipettor engaging a linear plurality of pipette tips along a different one of said axes.

6. The method of claim 4 in which the spacing of said pipette tips along said first axis is essentially 9.05 mm. on a center-to-center basis.

7. The method of claim 6 in which the spacing of said pipette tips in said tray along said second axis is about 9.8 mm. on a center-to-center basis.

8. The method of claim 4 in which said pipette tips are carried in said storage tray in a plurality of apertures defined in a wall, said apertures being arranged along said first axis with a spacing of 9.05 mm and along said second axis with a spacing of 9.8 mm., both on a center-to-center basis.

9. The method of claim 8 in which said first and second axes are perpendicular to each other.

* * * * *